United States Patent
Hahnl et al.

(10) Patent No.: US 10,857,373 B2
(45) Date of Patent: Dec. 8, 2020

(54) TREATMENT DEVICE FOR A TREATMENT USING A DIALECTICALLY IMPEDED PLASMA

(71) Applicant: CINOGY GMBH, Duderstadt (DE)

(72) Inventors: Mirko Hahnl, Berlingerode (DE); Karl-Otto Storck, Duderstadt (DE); Leonhard Trutwig, Duderstadt/Gerlingerode (DE); Dirk Wandke, Heilbad Heiligenstadt (DE); Matthias Kopp, Gieboldehausen (DE); Andreas Helmke, Einbeck (DE)

(73) Assignee: CINOGY GmbH, Duderstadt (DE)

( * ) Notice: Subject to any disclaimer, the term of this patent is extended or adjusted under 35 U.S.C. 154(b) by 246 days.

(21) Appl. No.: 15/580,959

(22) PCT Filed: Jun. 16, 2016

(86) PCT No.: PCT/DE2016/100274
§ 371 (c)(1),
(2) Date: Dec. 8, 2017

(87) PCT Pub. No.: WO2017/008781
PCT Pub. Date: Jan. 19, 2017

(65) Prior Publication Data
US 2018/0178024 A1    Jun. 28, 2018

(30) Foreign Application Priority Data

Jul. 14, 2015  (DE) .................. 10 2015 111 401

(51) Int. Cl.
*A61N 1/44* (2006.01)
*H05H 1/24* (2006.01)
(Continued)

(52) U.S. Cl.
CPC .............. *A61N 1/44* (2013.01); *A61L 2/14* (2013.01); *A61N 1/32* (2013.01); *H05H 1/2406* (2013.01);
(Continued)

(58) Field of Classification Search
CPC ... A61N 1/44; A61N 1/32; H05H 1/46; H05H 1/2406; H05H 2245/122;
(Continued)

(56) References Cited

U.S. PATENT DOCUMENTS 5,156,591 A    10/1992  Gross et al.
9,005,188 B2    4/2015  Wandke et al.
(Continued)

FOREIGN PATENT DOCUMENTS

DE    10 2009 060627 A1    6/2011
DE    10 2011 100751 A1    11/2012
(Continued)

*Primary Examiner* — Amber R Stiles
(74) *Attorney, Agent, or Firm* — W & C IP

(57) ABSTRACT

The invention relates to a treatment device for a surface to be treated using a dialectically impeded plasma, comprising a housing (1) which has an end wall (14, 14') and comprising an electrode (18, 33) which is shielded from the surface to be treated by a dielectricum (19, 34) that forms at least one part of the end wall (14, 14') and which can be connected to a high-voltage generator (17). The end wall (14, 14') has at least one spacer (29, 29') by means of which at least one gas chamber is formed when the at least one spacer (29, 29') rests against the surface to be treated, and the dialectically impeded plasma is formed in the gas chamber for the treatment process. The treatment device simultaneously allows a treatment using the dialectically impeded plasma and the metered supply of a treatment agent in that a storage chamber (25, 25') which can be filled with a treatment agent is arranged on the end wall (14, 14') face facing away from the surface to be treated; the end wall (14, 14') has passage
(Continued)

openings (28, 28'); and the volume of the storage chamber (25, 25') can be reduced such that the treatment agent reaches the region of the surface to be treated through the passage openings (28, 28') when the volume is reduced.

16 Claims, 11 Drawing Sheets

(51) Int. Cl.
- *H05H 1/46* (2006.01)
- *A61L 2/14* (2006.01)
- *A61N 1/32* (2006.01)
- *A61M 37/00* (2006.01)

(52) U.S. Cl.
CPC ....... *H05H 1/46* (2013.01); *A61M 2037/0007* (2013.01); *H05H 2001/2418* (2013.01); *H05H 2245/122* (2013.01)

(58) Field of Classification Search
CPC ........ H05H 2001/2418; H05H 2277/10; A61L 2/14; A61M 2037/0007
See application file for complete search history.

(56) References Cited

U.S. PATENT DOCUMENTS

| | | |
|---|---|---|
| 2003/0052096 A1* | 3/2003 | Crowe ................. H05H 1/2406 219/121.43 |
| 2013/0064726 A1 | 3/2013 | Morfill et al. |
| 2013/0345620 A1 | 12/2013 | Zemel et al. |
| 2014/0147333 A1 | 5/2014 | Morfill et al. |
| 2014/0207053 A1 | 7/2014 | Morfill et al. |
| 2015/0151135 A1 | 6/2015 | Kalghatgi et al. |
| 2015/0216026 A1 | 7/2015 | Wandke et al. |
| 2016/0236002 A1 | 8/2016 | Dirk et al. |
| 2016/0242269 A1 | 8/2016 | Dirk et al. |

FOREIGN PATENT DOCUMENTS

| | | |
|---|---|---|
| DE | 10 2012 015482 A1 | 2/2014 |
| DE | 10 2013 019057 A1 | 5/2015 |
| DE | 10 2013 019058 A1 | 5/2015 |
| EP | 2 170 022 A1 | 9/2008 |
| JP | 05-504711 A | 7/1993 |
| WO | 1992/10234 A1 | 6/1992 |

* cited by examiner

TREATMENT DEVICE FOR A TREATMENT USING A DIALECTICALLY IMPEDED PLASMA

The invention relates to a treatment device for a surface to be treated using a dielectric barrier plasma, comprising a housing which has an end wall and comprising an electrode which is shielded from the surface to be treated by a dielectric forming at least one part of the end wall and which can be connected to a high-voltage generator, wherein the end wall has at least one spacer by means of which at least one gas chamber is formed when the at least one spacer rests against the surface to be treated, and the dielectric barrier plasma is formed in the gas chamber for the treatment process.

DE 10 2009 060 627 B4 describes an electrode arrangement made of a planar, flexible electrode and a flexible, planar dielectric, in which the dielectric surrounds the planar electrode on all sides and only one connector of the electrode is routed out of the dielectric, in an insulating manner, for connection to a high-voltage generator. The dielectric is intended to be placed on the surface to be treated, for example the skin surface of a human or animal body, and includes a studded structure on the contact side, which functions as a spacer, because gas chambers can form between the studs, in which the dielectric barrier plasma can be formed.

A treatment device according to DE 10 2012 015 482 A1 is equipped with a similar electrode arrangement, wherein the dielectric embedding the electrode forms the end wall of a housing of a treatment device. The flexible electrode arrangement made of the flexible dielectric including the flexibly embedded, planar electrode is pressed against the surface to be treated by an elastic pressing means situated behind the electrode arrangement, whereby the adaptability of the electrode arrangement to contours of the surface to be treated, in particular the skin surface, is improved.

For cosmetic and medical purposes, in particular, a treatment using a dielectric barrier plasma is supported by an applied treatment agent. In the case of a cosmetic treatment of a skin surface, the treatment using the dielectric barrier plasma effectuates both a cleaning/disinfecting of the surface as well as an improved circulation and dilation of the pores, and therefore a treatment agent can be efficiently absorbed by the skin. In the non-cosmetic field, a treatment agent, such as, for example, a primer or an impregnating agent, can be better applied onto a wood or plastic surface after a plasma treatment, since the adhesion of this treatment agent on the surface improves. It is common to apply the treatment agent in a separate step before or after the plasma treatment.

The problem addressed by the present invention is that of designing a treatment device of the type mentioned at the outset in such a way that an improved treatment using a dielectric barrier plasma is possible with the use of a treatment agent, in particular a cosmetic treatment of the skin surface.

In order to solve this problem, according to the invention, a treatment device of the type mentioned at the outset is characterized in that a storage chamber, which is fillable with a treatment agent, is situated on the side of the end wall facing away from the surface to be treated, the end wall includes passage openings, and the volume of the storage chamber can be reduced in such a way that the treatment agent reaches the region of the surface to be treated through the passage openings when the volume is reduced.

The treatment device according to the invention therefore makes it possible to apply the treatment agent onto the surface to be treated also during the treatment using the dielectric barrier plasma, and therefore the effect of plasma and treatment agent on the surface to be treated can take place simultaneously and with a continuous resupply of the treatment agent.

In one preferred specific embodiment of the invention, the application of the treatment agent, i.e., the reduction of the storage chamber, is carried out by applying a pressure onto the surface to be treated. The application of the treatment agent can therefore take place uniformly by way of a uniform application of pressure onto the surface to be treated.

In a first structural embodiment suited for this purpose, the housing comprises peripheral wall sections which engage telescopically into each other and can be slid into each other by applying pressure onto the housing in the direction of the surface to be treated, whereby the treatment agent emerges through the passage openings of the end wall.

In yet another structural embodiment of this principle, the end wall is designed to be at least partially flexible and is deformed in the direction of the interior of the storage chamber by an application of pressure onto the housing in the direction of the surface to be treated, whereby the volume reduction takes place in order to apply the treatment agent.

In yet another structural embodiment, the housing comprises flexible peripheral walls which delimit the storage chamber and can be pressed inward in order to reduce the volume of the storage chamber. The peripheral walls can be pressed inward both by applying a radially inwardly oriented pressure onto the peripheral walls and by applying an axial pressure in in the direction of the surface to be treated when the peripheral wall dents inward as a result.

Due to the reduction of the volume of the storage chamber, the treatment agent is pressed through the passage openings of the end wall of the housing into the region of the surface to be treated. Apparently, the treatment agent must be free-flowing for this purpose. This is the case when the treatment agent is powdery, paste-like, gaseous, or liquid in the suitable form. Expediently, the internal diameters of the passage openings are adapted accordingly. In the case in which a powdery treatment agent is expelled, larger passage openings can be used than for paste-like or viscous treatment agents, while highly fluid or gaseous treatment agents are usefully applied through passage openings having a small inner cross-section.

In one structural embodiment of the treatment device according to the invention, the electrode is embedded, as a planar electrode, on all sides in the dielectric which is designed to be planar. Since the dielectric surrounds the planar electrode on all sides, the electrode must also comprise passage openings. According to the invention, however, these passage openings are larger than the passage openings of the dielectric, and so passage channels are formed in the dielectric, which are continuously radially delimited from the dielectric, and therefore an unwanted current flow via the treatment agent is reliably avoided.

It can be expedient for the invention when the arrangement comprising dielectric and embedded electrode is designed to be flexible.

The dielectric can extend across the entire end wall, and so the end wall is formed by, the dielectric. In this case, the flexible embodiment of the arrangement comprising dielectric and embedded electrode is advantageous in order to allow for an adaptation to uneven contours of the surface to be treated.

In yet another structural embodiment of the invention, the end wall is formed as at least two parts. In particular, in this case, a first part of the end wall can be formed by dielectric shielding of the electrode and at least one second part of the end wall can delimit the storage chamber and can comprise the passage openings. The above-described possibilities for reducing the volume of the storage chamber in order to apply the treatment agent can also all be utilized for this embodiment and can be selected depending on the application and the expediency.

It can be advantageous when the dielectric forms central section of the end wall and the second part of the end wall annularly surrounds the dielectric and, therefore, the electrode embedded into the dielectric. In this case, it can be sufficient when the second part of the end wall is flexible, while the central arrangement made of the dielectric and the electrode shielded by the dielectric is hard, i.e., is inflexible with respect to the pressures applied in practice for the treatment.

The at least one second part of the end wall can consist of an insulating plastic, i.e., more or less continue the dielectric in the end wall also outside the region of the electrode. In this structural embodiment, the formation of the at least one second part of the end wall of an insulating material is not absolutely necessary, and therefore materials having a moderate or high conductivity can also be utilized.

In this case, it can be expedient when the at least one second part of the end wall forms the at least one spacer, by means of which the arrangement comprising dielectric and electrode is held at a close distance to the surface to be treated when the at least one spacer rests against the surface to be treated. As a result, a small intermediate space forms between the dielectric shielding the electrode and the surface to be treated. The dielectric barrier plasma forms in this gas chamber or air chamber via ionization of the gas or air that is present there, wherein a direct current flow between the surface to be treated and the electrode is impeded by the dielectric, and therefore only displacement currents are possible for the plasma formation. This also applies, of course, for the arrangement in which the dielectric itself is formed with at least one spacer, and therefore a gas chamber or air chamber of this type exists between the deepened region of the dielectric (outside of the at least one spacer) and the surface to be treated. A direct current flow between the electrode and the surface to be treated is impeded in this case as well.

The plasma formation can take place using a DC high voltage, wherein only an initial displacement current results and the potential difference maintains the plasma. The use of an AC high voltage is preferred, however, wherein the high-voltage potential switches between a positive voltage and a negative voltage. It is preferred, in this case, that the surface to be treated, for example the skin surface or the body of the living being, functions as a so-called floating counterelectrode which could only sluggishly follow the change in potential of the AC voltage and, therefore, due to the changing frequency, essentially remains at an average potential which will become the ground potential.

It is expedient to not fill the treatment agent directly into the storage chamber, in particular when a paste-like or liquid treatment agent is utilized. In this case, it is expedient to introduce the treatment agent into the storage chamber in a carrier material. The carrier material can be any loose material which is compressible by way of the reduction of the volume of the storage chamber, such as, for example, a cotton material, a non-woven material, or an open-pored sponge material. In this case, the treatment agent is pressed out of the carrier material when the volume of the storage chamber is reduced in at least one of the described ways.

A particularly advantageous embodiment of the invention results from the fact that a housing part comprising an end wall and at least one part of the storage chamber is designed as an exchangeable headpiece. The headpiece stores the treatment agent in a quantity, in this case, which is provided for a treatment of a surface, for example for a cosmetic facial. After the treatment agent has been used up and the treatment has ended, the exchangeable headpiece can be removed and the treatment device according to the invention can be made usable again by means of a new headpiece. In this way, a high hygienic standard is ensured, which requires no cleaning measures or only minor cleaning measures which are easy to carry out.

The invention is described in greater detail in the following with reference to exemplary embodiments represented in the drawings. In the drawings.

Figure 1:
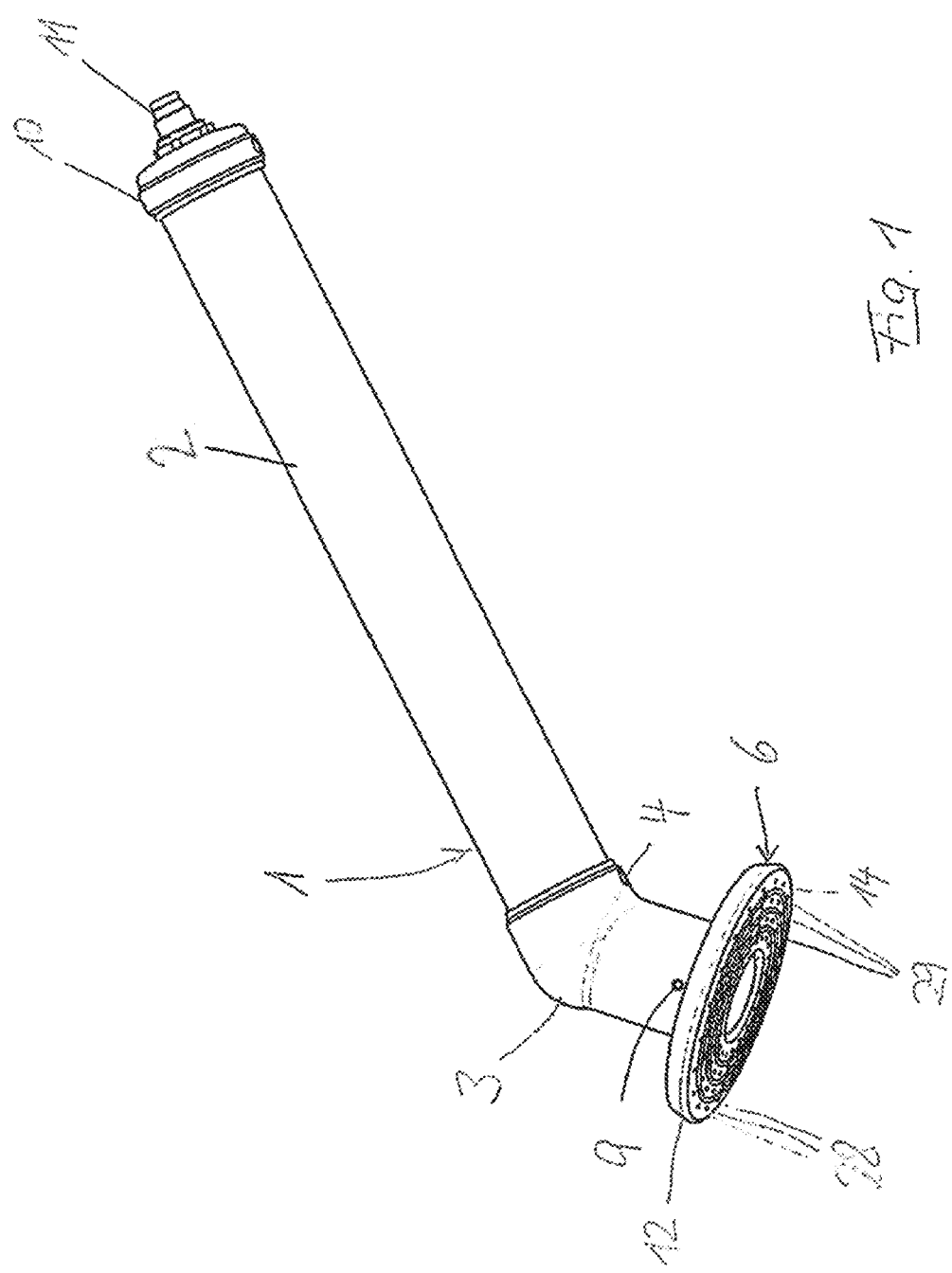
FIG. 1 shows a view of a first embodiment of a treatment device according to the invention in the assembled state.
Figure 2:
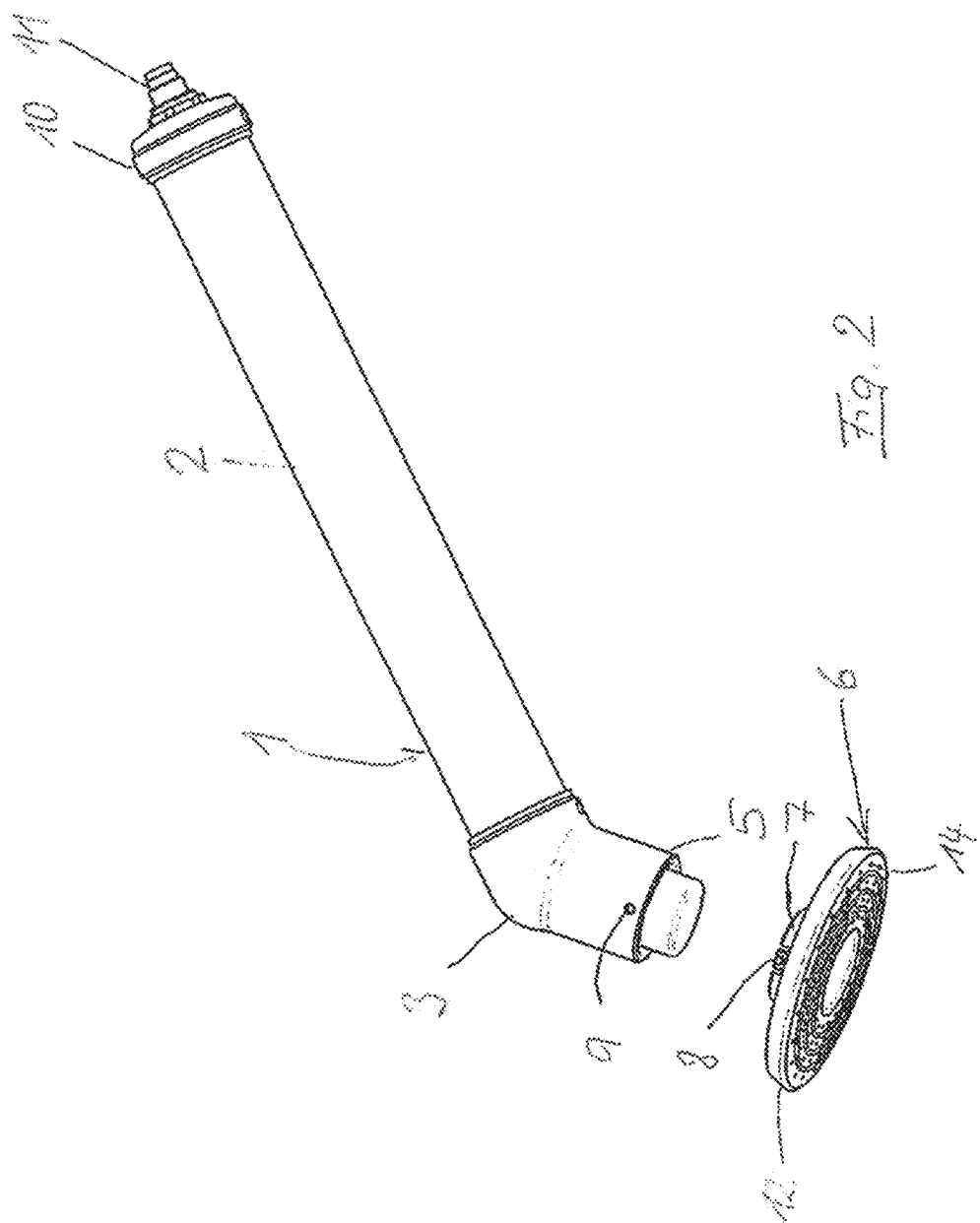
FIG. 2 shows the view according to FIG. 1 with headpiece removed.

The treatment device according to a first embodiment of the invention, which is represented in FIG. 1, comprises a housing 1 which consists of a handle 2 and an angle piece 3. The two housing parts are designed as hollow tubes, wherein the handle 2 is a straight hollow tube and the angle piece 3 has two tube ends connected to each other at an angle of approximately 135°. The handle 2 and the angle piece 3 are connected to each other in that the angle piece 3 comprises an insertion receptacle for the hollow tube, of the handle 2. The handle 2, which has been slid into the angle piece 3, is fixed in the installed state by means of a screw 4. The handle 2 can be formed as a drawn tube made of plastic or metal, while the angle piece 3 is preferably an injection-molded part. A headpiece 6 including a tubular shoulder 7 can be inserted into the end 5 of the angle piece 3 facing away from the handle 2. The tubular shoulder 7 comprises two diametrically opposed, resilient detent pins 8, each of which can engage into a detent opening 9 in the tubular end 5 of the handle 2 for fixing the headpiece 6 on the angle piece 3, whereby a secured connection in the axial direction and with respect to rotation is established.

The end of the handle 2 that is not connected to the angle piece 3 is closed by an end cap 10 including a cable bushing 11. The end cap 10 is preferably screwed onto a thread of the handle 2.

The headpiece 6 comprises a peripheral wall 12 which is connected to the tubular shoulder 7 via a connecting wall 13 extending essentially perpendicularly to the tube axis. The free peripheral edge of the peripheral wall 12 is closed by means of an end wall 14. In the exemplary embodiment represented, the headpiece 6 is essentially circular cylindrical, and therefore the end wall 14 fills a circular surface.

Figure 3:
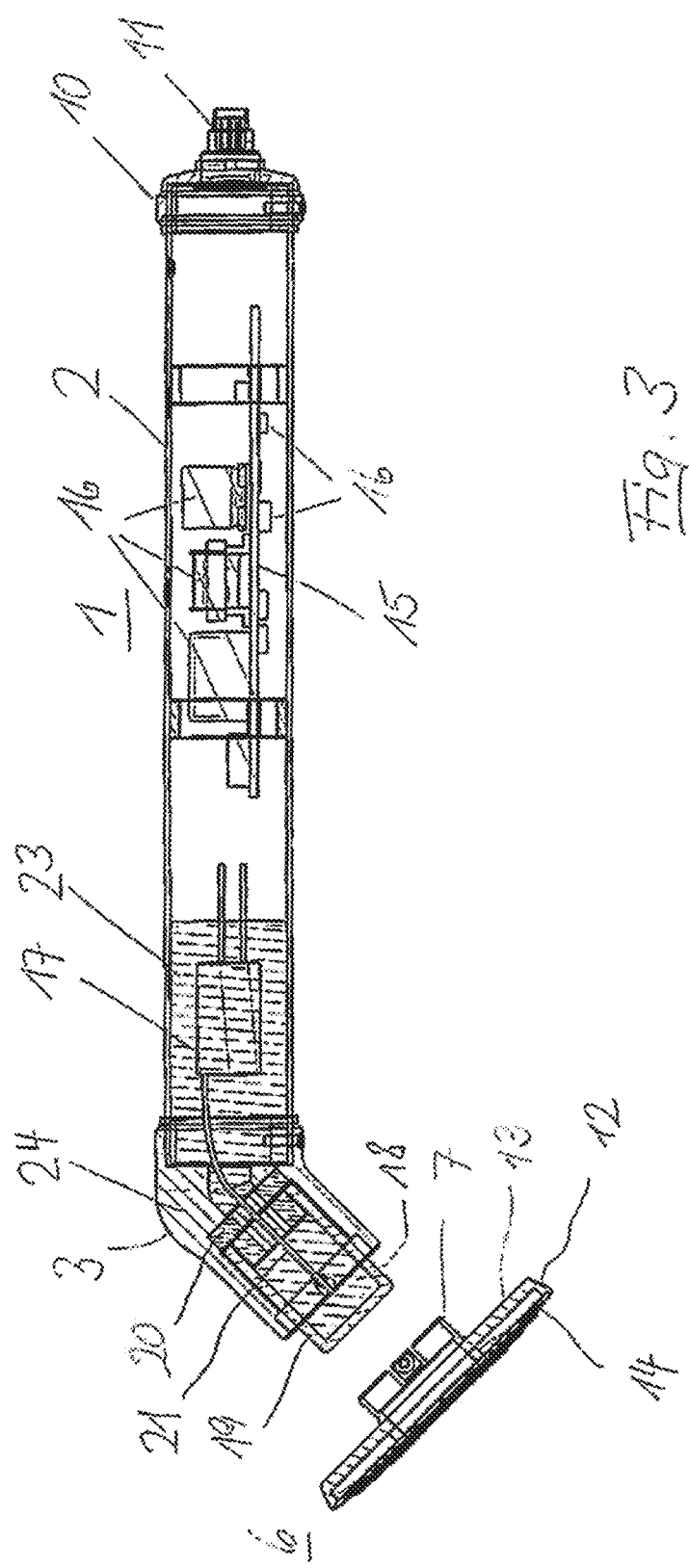
FIG. 3 shows a sectional representation of the treatment device according to FIG. 2.
Figure 4:
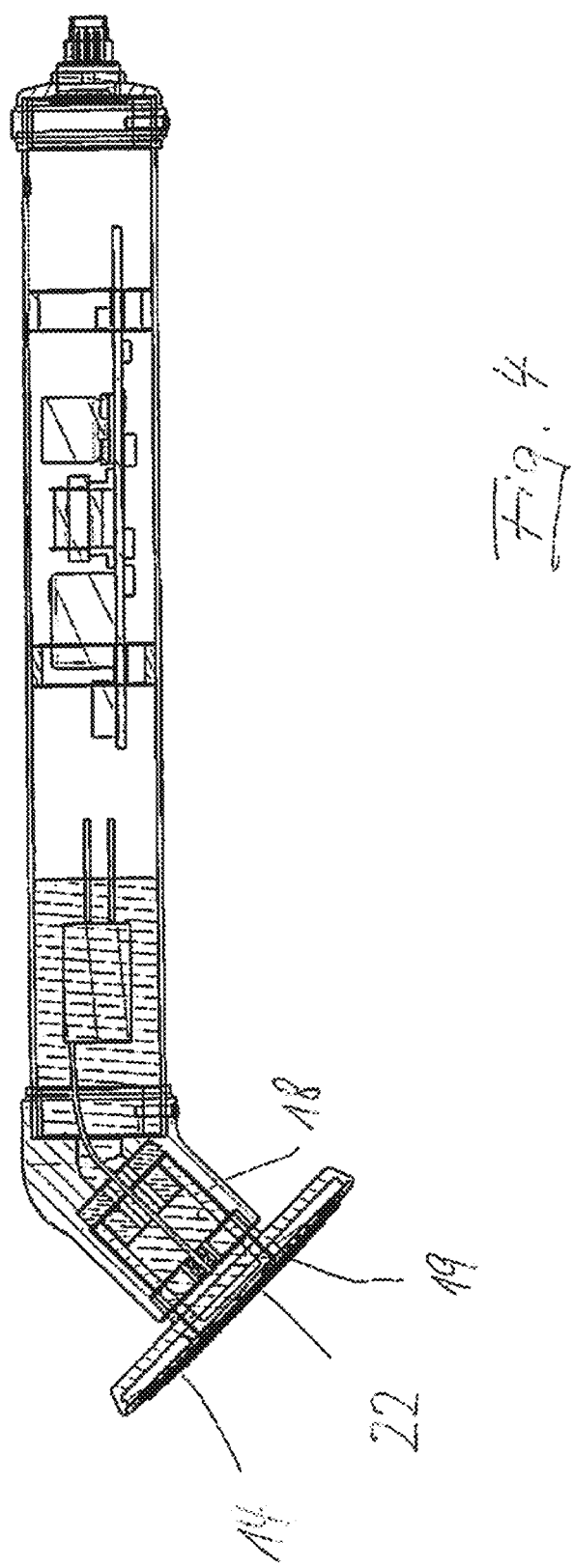
FIG. 4 shows a sectional representation of the fully assembled treatment device according to FIG. 1.

FIGS. 3 and 4 show the inner design of the housing 1, wherein the headpiece 6 is represented separately in FIG. 3, while, in FIG. 4, the headpiece 6 is coupled to the angle piece 3 by means of the detent connection comprising detent pin 3 and detent opening 9.

As schematically represented in FIGS. 3 and 4, a circuit board 15 is located in the interior of the handle 2, on which components 16 for an electric control are located. The circuit board 15 is connected to a mains alternating current via a cable (not represented) which is routed through the cable bushing 11 in the end cap 10 of the housing 1. A rectified voltage is fed via a connection (not shown) to an inverter 17 which is suitable for generating, in a known way, a high voltage which is fed as an AC high voltage to a solid, cylindrical electrode 18. The electrode 18 is surrounded by a pot-shaped dielectric 19 which, in the interior of the angle piece 3, abuts an insulating bushing 20 for a high-voltage line 21.

Figure 6:
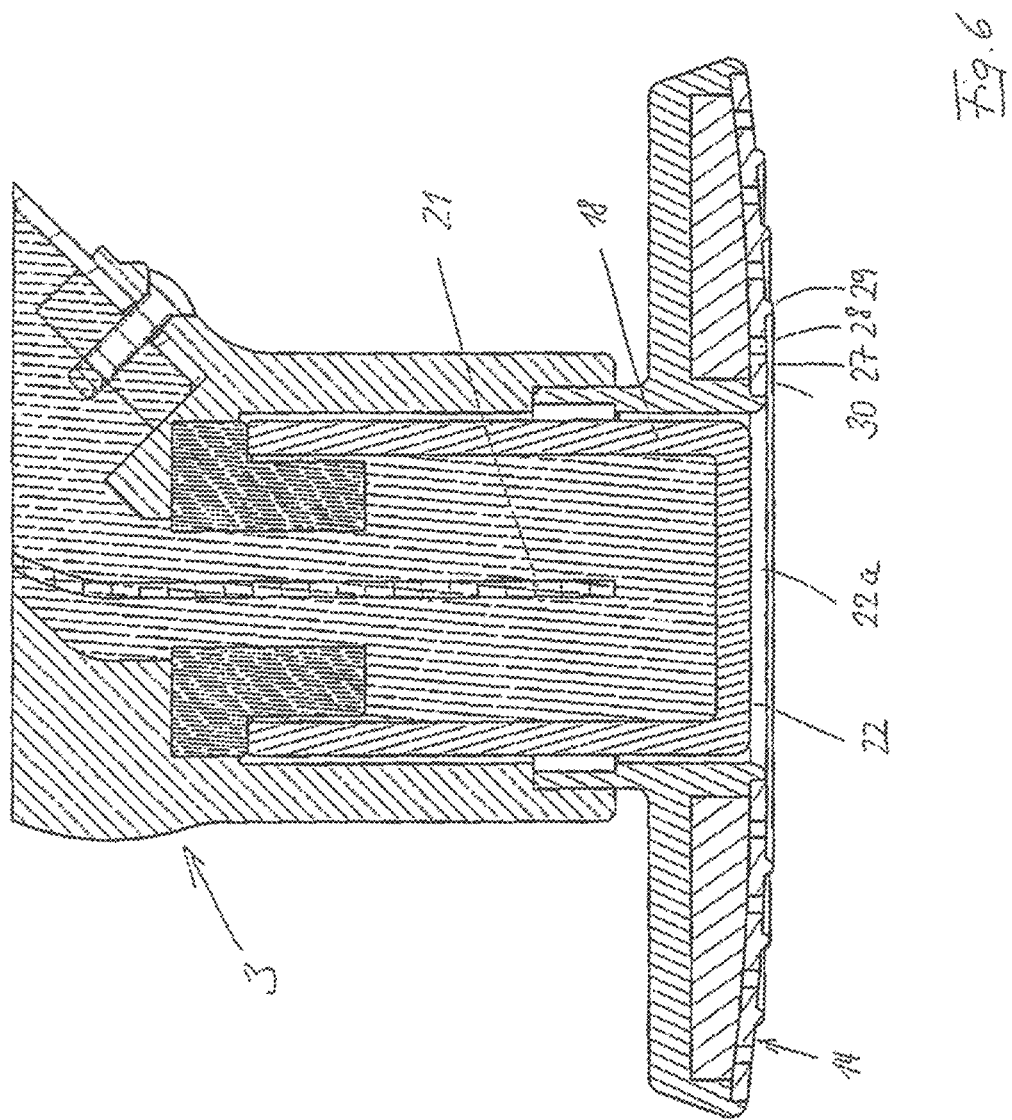
FIG. 6 shows a representation according to FIG. 5 after the headpiece has been inserted into the rest of the housing.

As illustrated in FIG. 4, the electrode 18 including the dielectric 19 extends into the region of the end wall 14 to such an extent that a small intermediate space remains between the underside of the base 22 and the underside of the end wall 14; the intermediate space is represented in greater detail in FIG. 6.

FIGS. 3 and 4 show that the region of the circuit, in which the high voltage is generated and the high voltage is forwarded to the electrode 18, is completely filled with a sealing compound 23, 24 in the interior of the handle 2 and the angle piece 3 in order to ensure an additional security against a high voltage flashover.

Figure 5:
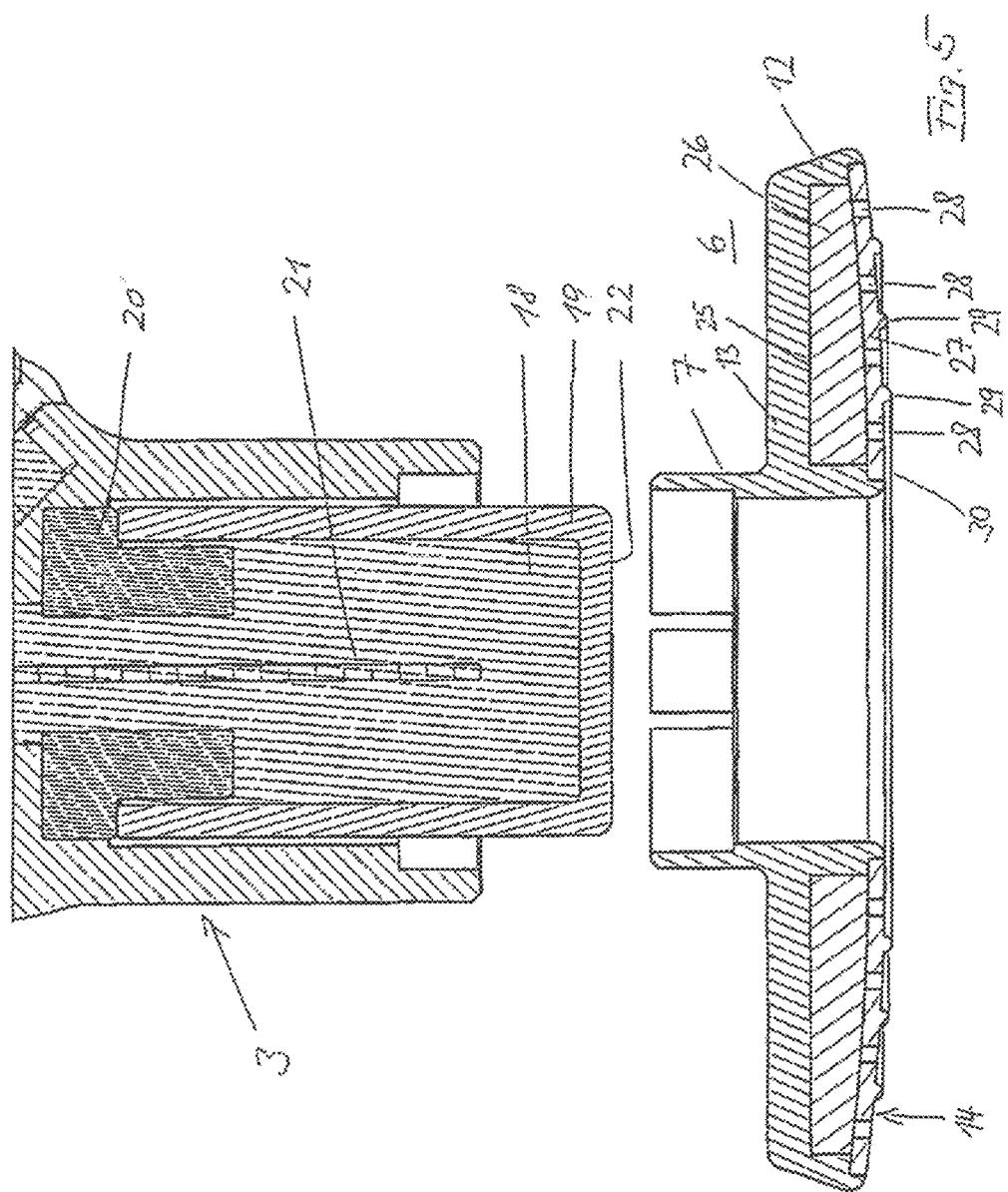
FIG. 5 shows an enlarged representation of the design of the headpiece and one end of the rest of the housing in a separate position.

FIGS. 5 and 6 illustrate the specific design of the headpiece 6, the peripheral wall 12, and the end wall 14 in relation to the end of the angle piece 3 in a separate representation and in the assembled state, respectively. In this case, it becomes clear that the tubular shoulder 7 extends up to the end wall 14, and therefore an annular storage chamber 25 is delimited by the tubular shoulder 7, the connecting wall 13, the peripheral wall 12, and the end wall 14, which storage chamber is filled with a carrier material 26 which is impregnated with a treatment agent and is in the form of a sponge-like annular body. As is apparent in FIG. 6 in particular, the end wall 14 is centrally formed by the base 22 of the dielectric 19 as the first part of the end wall 14, while a second part of the end wall 14 abuts radially outwardly, which second part consists of an annular, planar wall piece 27 which is held radially inwardly by the tubular shoulder 7 and radially outwardly by the peripheral wall 12. In the exemplary embodiment represented, this planar wall piece 27 consists of en insulating plastic and comprises numerous passage openings 2 the arrangement of which on the end wall 14 is apparent in FIG. 1. Furthermore, integrally formed, annular ribs which are used as spacers 29 are located on the underside of the wall piece 27. The wall piece 27 consists of a flexible material which can be deformed into the region of the storage chamber 25 by means of a pressure applied onto a surface to be treated (not shown), and therefore the volume of the storage chamber 25 and of the carrier material located therein is reduced. By way of the compression of the carrier material, the treatment agent contained therein is pressed through the passage openings 28 and reaches the region of the surface to be treated, between the spacers 29. Due to the spacers 29, a surface 30 of the well piece 27 results, which is offset with respect to the spacers 29 and aligns with the underside of the base 22 of the dielectric 19. The height of the spacers 29 therefore determines the height of the intermediate space 22a between the base 22 of the dielectric 19 and the surface to be treated. The dielectric barrier plasma forms in this intermediate space when a high voltage is applied to the electrode 18, wherein the surface to be treated, for example the skin surface of a human or animal body, is used as a floating counterelectrode. It goes without saying that the invention also does not rule out that the body—and, therefore, the surface to be treated—are grounded in order to reduce a float of the potential of the surface to be treated, as the counterelectrode.

It is apparent, in this exemplary embodiment, that the dielectric 19 tightly surrounds a rigid electrode 18, and therefore the end wall 14 is inflexible in the region of the dielectric 19. The center of the end wall is therefore rigid, while the second part of the end wall 14 surrounding the dielectric 19, in the form of the wall piece, is flexible and can adapt, within limits, to contours of the surface to be treated. The reduction of the volume of the storage chamber 25, by way of which the treatment agent is pressed through the passage openings 28 into the region of the surface to be treated, takes place by way of an indentation of the wall piece 27 into the interior of the storage chamber 25 when a handling pressure is applied onto the surface to be treated by means of the housing 1 including the handle 2. The volume of the storage chamber 25 is selected in such a way that the quantity of treatment agent required for an intended treatment, for example a cosmetic facial, can be pressed through the passage openings 28 during the treatment. After the end of the treatment, the headpiece 6 can be removed from the angle piece 3 by means of the detent pins 8 and exchanged for a new headpiece 6 filled with a suitable treatment agent, and therefore the headpiece 6 can be used as a disposable piece and can be subsequently discarded. It is apparent that only the smooth underside of the dielectric 19 must be cleaned, which is possible without problems, however, due to the smooth surface.

FIGS. 5 and 6 also show that the flexible wall piece 27 can be installed in an approximately pre-curved shape, whereby a pressing-in into the volume of the storage chamber 25 takes place even when a slight amount of handling pressure is applied, and the treatment agent is pressed through the passage openings 28 into the region of the surface to be treated already at the beginning of the treatment.

Figure 7:
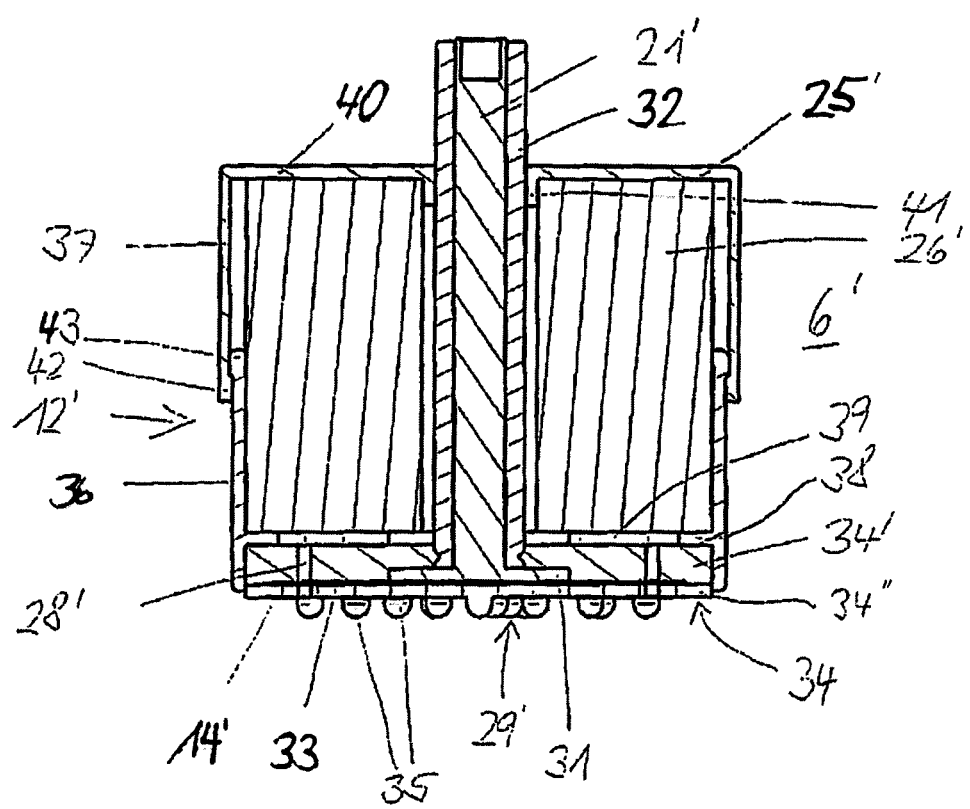
FIG. 7 shows a sectional representation of a headpiece of a treatment device according to a second embodiment of the invention.

A headpiece 6' of another embodiment of a housing according to the invention is represented in FIGS. 7 to 12. FIG. 7 shows a vertical section through the headpiece 6'. The coupling of the headpiece 6' to the angle piece 3 takes place in a modified way via a solid, metallic, high-voltage connecting piece 21' in the form of a cylindrical bolt which transitions, at the lower end, into a circular, solid flange 31. The bolt of the metallic connecting piece 21' is surrounded by a tightly fitting, insulating tube piece 32 which extends up to the flange 31. A planar, flexible electrode 33, which is completely embedded into a dielectric 34, rests against the underside of the flange 31. The dielectric extends on all sides beyond the edge of the electrode 33 and consists of two planar layers 34', 34" which cover the electrode 33 on both surfaces and are fixedly connected to each other radially outside, the electrode 33, for example by means of adhesive bonding or welding. The dielectric 34 forms an end wall 14'. The surface of the end wall 14' is formed by the lower layer 34" of the dielectric which is provided with protruding studs 35 as spacers 29' which are integral with the lower layer 34" of the dielectric. The dielectric comprises a plurality of passage openings 28', of which only two are apparent in the sectional representations in FIGS. 7 to 9. The distribution of the passage openings 28' over the end wall 14' becomes apparent by way of the view in FIG. 11, which also illustrates the position of the numerous studs 35 forming the spacers 29' in this exemplary embodiment.

The end wall 14' is delimited on its radial edge by a peripheral wall 12' which is formed by a lower peripheral wall section 36 and an upper peripheral wall section 37. The peripheral wall sections 36, 37 are circular cylindrical and engage telescopically into each other. An intermediate base 38, which rests on the top side of the dielectric 34, extends radially inwardly from the lower peripheral wall section 36. The intermediate base 38 is provided with large passage openings 39. The upper peripheral wall section 37 transitions into a horizontal cover wall 40 which extends up to the insulating tube 32 and transitions there into a downwardly directed, tubular section 41 which slidingly rests against the insulating tube 32.

The peripheral wall sections 36, 37 engage telescopically into each other and each comprise, on their overlapping ends, an annular bead 42, 43, wherein the annular bead 42 on the upper, outer peripheral wall 37 is directed inwardly and the annular bead 43 on the end of the inner, lower peripheral wall section 36 is directed outwardly. As a result, the annular beads 42, 43 prevent the peripheral wall sections 36, 37 from being pulled apart from each other, beyond the starting position depicted in FIG. 7, during the treatment process.

An annular storage chamber 25' is delimited by the cover wall 40 having the tubular section 41, the peripheral wall sections 36, 37 which telescopically engage into each other, and the intermediate base 38, in which storage chamber, in turn, a carrier material 26' impregnated with a treatment agent is situated. By means of a pressure applied onto the surface to be treated (not shown) and against which the studs 35 rest, as spacers 29', the upper peripheral wall section 37 is moved downward relative to the lower peripheral wall section 36, and therefore the volume of the storage chamber 25' is reduced and the carrier material 26' is compressed. As a result, treatment material emerges from the carrier material 26' through the passage openings 39 of the intermediate base 39 and the passage openings 28' of the dielectric into the region of the surface to be treated, which is kept free, as an air chamber, by means of the spacers 35 between the surface to be treated and the surface 30' which is offset with respect to the spacers 29', and in which the dielectric barrier plasma can form.

Figure 8:
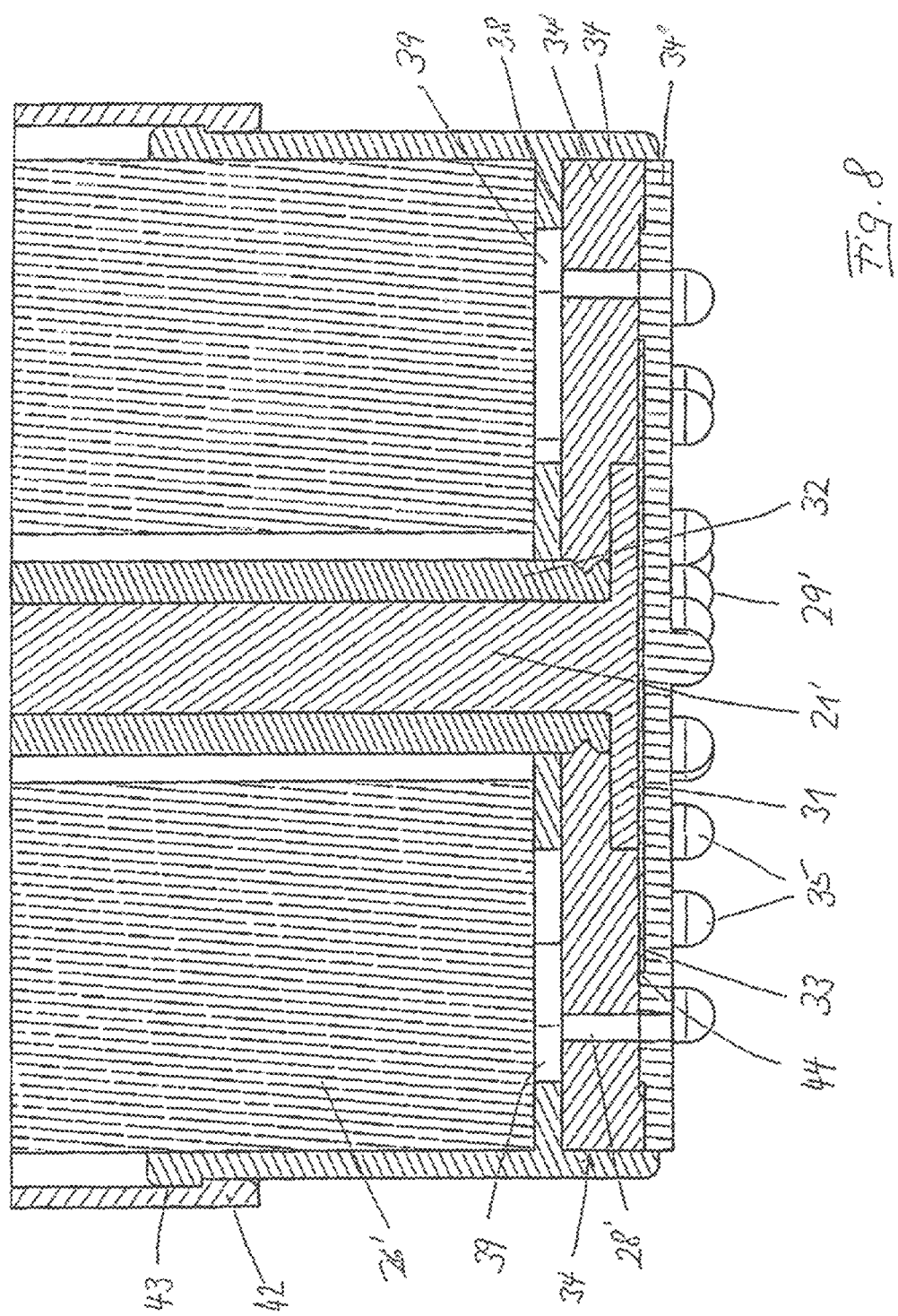
FIG. 8 shows an enlarged cutout representation of the lower part of the headpiece according to FIG. 7.

FIG. 8 illustrates, in particular, that substantially larger passage, openings 44 of the electrode 33 align with the passage openings 28' of the dielectric 34. When the two layers 34', 34" of the dielectric are connected, the dielectric fills the passage openings 44 of the electrode 33 up to the internal diameter of the passage opening 28', and therefore a passage channel results, which is continuously delimited from the dielectric 34, wherein direct contact between the treatment agent and the electrode 33 becomes impossible.

Figure 9:
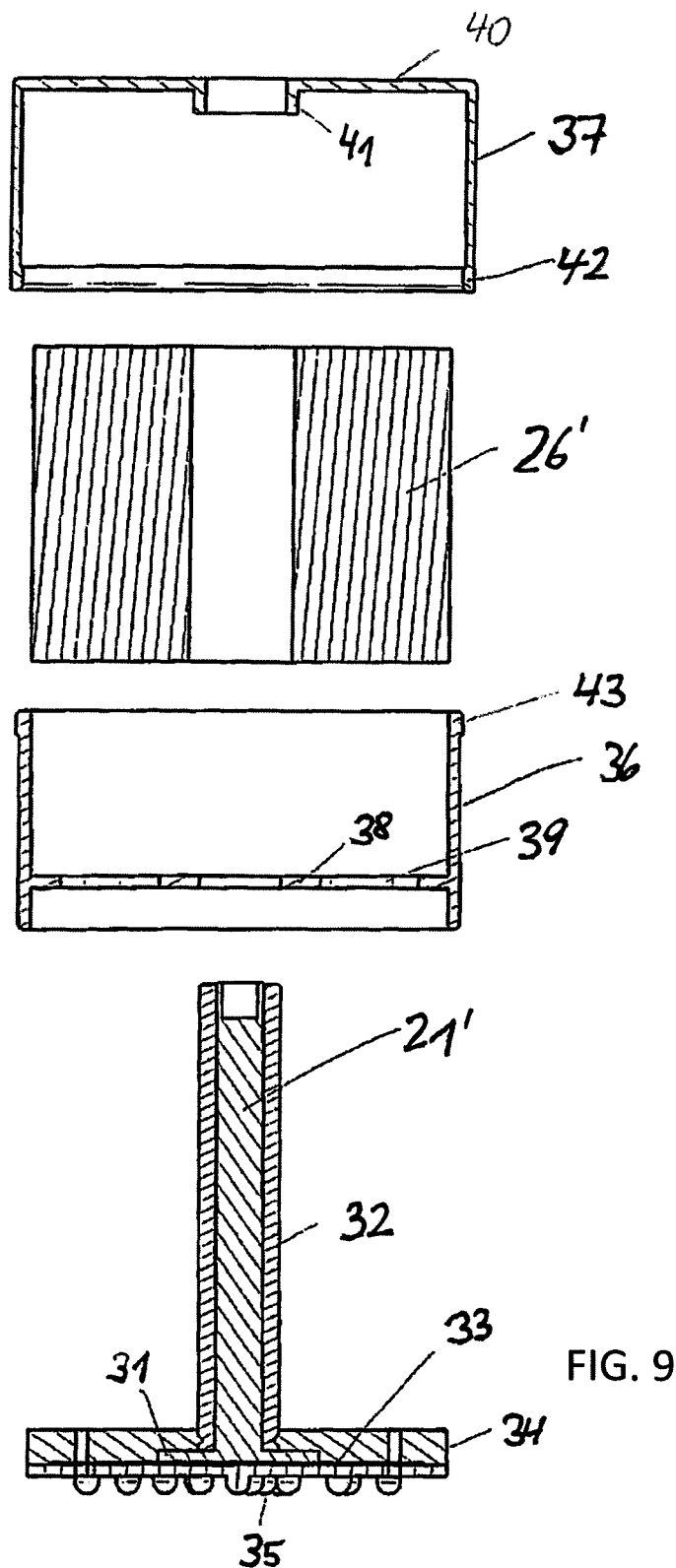
FIG. 9 shows an exploded representation of the headpiece according to FIG. 7.

FIG. 9 illustrates the individual parts of the headpiece 6' in an exploded representation.

Figure 10:
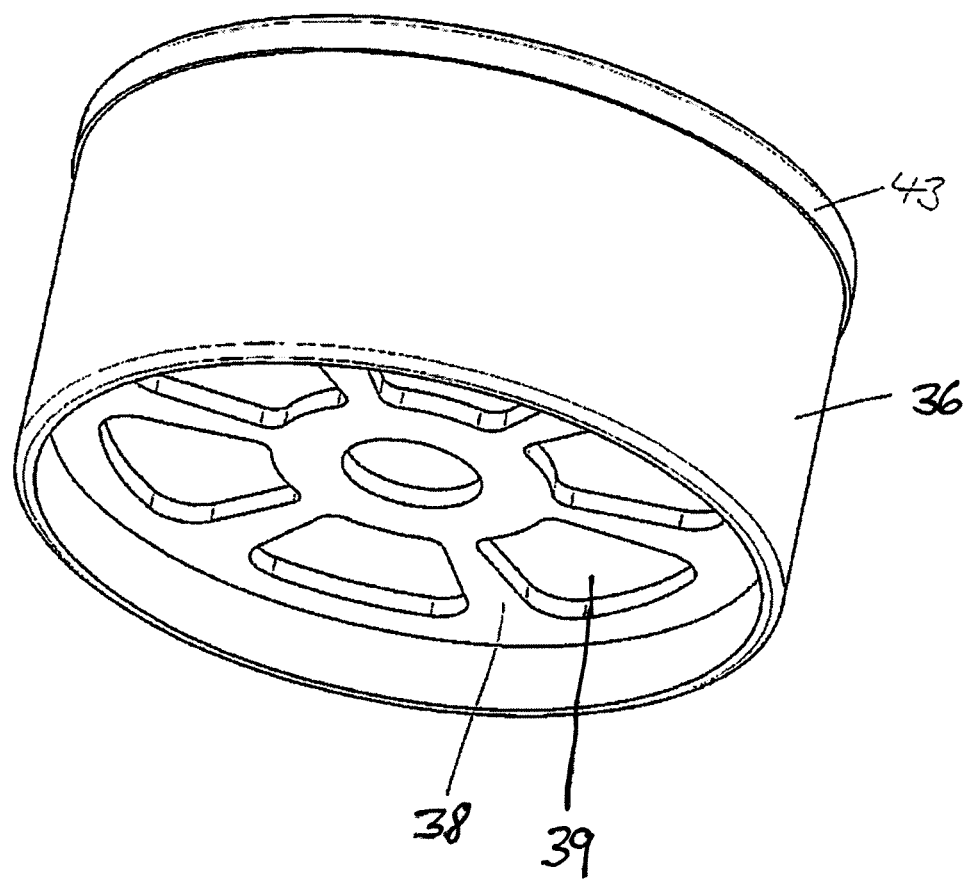
FIG. 10 shows a perspective top view of an intermediate piece including a peripheral wall section of the housing.
Figure 11:
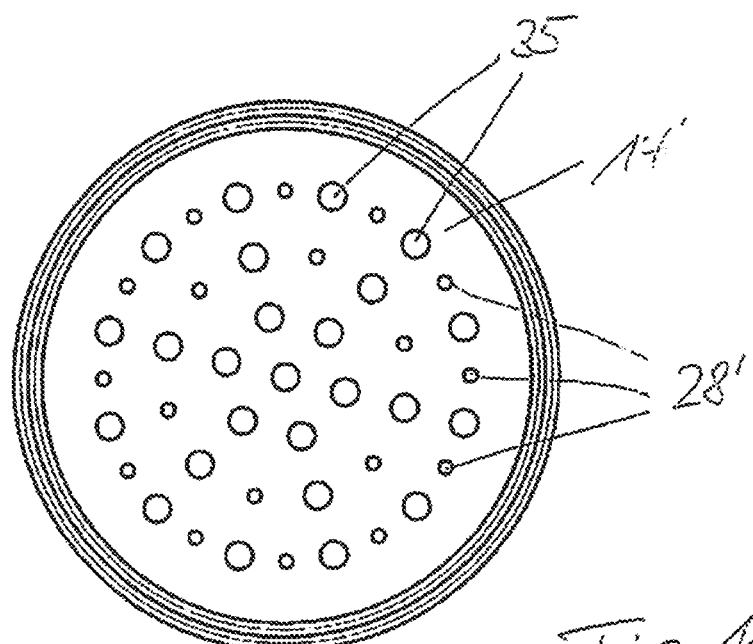
FIG. 11 shows a top view of the end wall the treatment device according to FIG. 7.

FIG. 10 shows an injection-molded part including the lower peripheral wall section 36, the annular bead 43, and the intermediate base 38, and illustrates the size of the passage openings 39 which are not to impede an emergence of the treatment agent from the storage chamber 25'.

Figure 12:
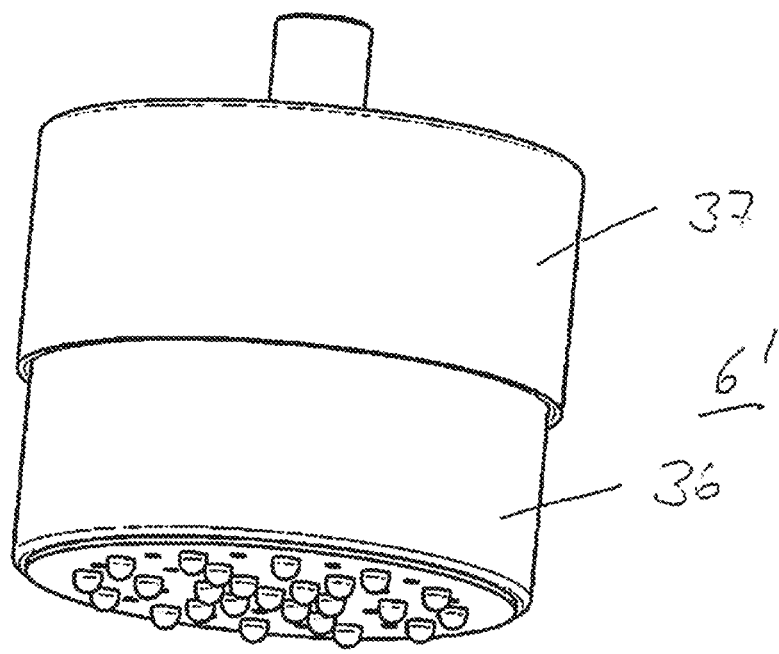
FIG. 12 shows a perspective view of the headpiece according to FIG. 7.

FIG. 12 shows a perspective view, obliquely from below, of the headpiece according to this embodiment, in which the upper peripheral wall section 37 is downwardly displaceable with respect to the lower peripheral wall section 36, and therefore the volume of the storage chamber 25' is reduced by means of a pressure applied onto the surface to be treated.

In yet another embodiment, the headpiece 6' could be formed having a uniform peripheral wall which, however, cannot be pressed radially inwardly. As a result, the reduction of the volume of the storage chamber 25' could be effectuated by way of finger pressure directed radially inwardly onto the peripheral wall. In this way as well, the treatment agent could be pressed out of the storage chamber 25 in the region of the surface to be treated. One variant of this embodiment can also provide, alternatively or additionally, a flexible cover wall 40.

The headpiece 6' can also be provided as an exchangeable part after a treatment. Due to the volume of the storage chamber 25', which is greater, in principle, this headpiece 6' can be provided for a substantially larger treatment. When the headpiece 6' is exchanged, a headpiece 6' including another treatment agent can also be provided, of course. In the case of cosmetic or medical treatments, for example, it is possible to initially work with a highly effective treatment agent and, when the starting state has improved, to transition to a milder treatment agent. This step can be repeated, of course, in order to transition to an even milder treatment agent. Finally, it is possible to utilize an agent that is only nurturing as the treatment agent.

It is readily apparent to a person skilled in the art that the exemplary embodiments shown represent different mechanisms for the reduction of the volume of the storage chamber 25, 25', each in combination with a certain design of the end wall 14, 14', but that the different methods for reducing the volume can be arbitrarily combined with the embodiment of the end wall 14, 14' formed as one part or as multiple parts. In this way, it is possible to provide the embodiment of the headpiece 6' with peripheral wall sections 36, 37, which can be telescopically slid into each other, in the case of an end wall 14, in which the electrode is located only in the region of a central dielectric, and an annular wall piece, which comprises the passage openings 28, is provided radially around the dielectric.

In the same way, the end wall 14' can be completely formed by the dielectric 34 which, however, can be deformed, including the embedded flexible electrode 33, by way of the pressure applied onto the surface to be treated, and, in this way, effectuates a reduction of the volume of the storage chamber 25, 25'.

The invention claimed is:

1. A treatment device for a surface to be treated using a dielectric barrier plasma, comprising:
   a housing which has an end wall;
   an electrode which is shielded from the surface to be treated by a dielectric that forms at least one part of the end wall wherein the electrode is connectable to a high-voltage generator,
   wherein the end wall has at least one spacer which forms at least one gas chamber when the at least one spacer rests against the surface to be treated, and wherein the dielectric barrier plasma is formed in the gas chamber; and a storage chamber fillable with a treatment agent arranged on a side of the end wall facing away from the surface to be treated, wherein the end wall has passage openings, and wherein a volume of the storage chamber can be reduced in such a way that upon a reduction of said volume the treatment agent reaches a region of the surface to be treated through the passage openings when the volume is reduced.

2. The treatment device as claimed in claim 1, wherein the reduction of the volume of the storage chamber takes place by applying a pressure onto the surface to be treated with the housing.

3. The treatment device as claimed in claim 1, wherein the housing comprises peripheral wall sections which telescopically engage into each other and which can be slid relative to each other for the reduction of the volume by way of pressure applied onto the housing in the direction of the surface to be treated.

4. The treatment device as claimed in claim 1, wherein the end wall is at least partially flexible and deforms in a direction of an interior of the storage chamber by way of pressure applied onto the housing in the direction of the surface to be treated.

5. The treatment device as claimed in claim 1, wherein the housing comprises a flexible peripheral wall which delimits the storage chamber and wherein upon pressing the flexible peripheral wall inward the volume of the storage chamber is reduced.

6. The treatment device as claimed in claim 1, wherein the electrode is a planar electrode, and is embedded on all sides into said dielectric formed as a planar dielectric, and wherein the passage openings in the end wall are in the dielectric and are smaller than corresponding passage openings of the electrode such that passage channels are formed from the passage openings in the end wall and the corresponding passage openings of the electrode and are continuously radially delimited by the dielectric.

7. The treatment device as claimed in claim 6, wherein an arrangement comprising the electrode embedded in the dielectric is flexible.

8. The treatment device as claimed in claim 1, wherein said dielectric extends as one piece over the entire end wall.

9. The treatment device as claimed in claim 1 wherein the end wall is in the form of at least two parts.

10. The treatment device as claimed in claim 9, wherein a first part of the at least two parts of the end wall is formed by said dielectric of the electrode and at least one second part of the at least two parts of the end wall delimits the storage chamber and includes the passage openings.

11. The treatment device as claimed in claim 10, wherein the dielectric forms a central section of the end wall and the at least one second part annularly surrounds the dielectric.

12. The treatment device as claimed in claim 10 wherein the at least one second part consists of an insulating plastic.

13. The treatment device as claimed claim 10 wherein the at least one second part forms the at least one spacer.

14. The treatment device as claimed in claim 1 wherein the treatment device is configured such that surface to be treated functions as a counterelectrode to the electrode.

15. The treatment device as claimed in claim 1 wherein a housing part of the housing which comprises the end wall and at least one part of the storage chamber are configured as an exchangeable headpiece.

16. The treatment device as claimed in claim 1 wherein the treatment device is configured such that the treatment agent is introduceable into the storage chamber in a carrier material.

* * * * *